US006255104B1

(12) United States Patent
Bertling

(10) Patent No.: US 6,255,104 B1
(45) Date of Patent: Jul. 3, 2001

(54) RECOMBINANT POLIOVIRUS VECTOR AND METHOD OF PREPARING THE SAME

(76) Inventor: Wolf Bertling, Meisenweg 22, 91056 Erlangen (DE)

(*) Notice: Subject to any disclaimer, the term of this patent is extended or adjusted under 35 U.S.C. 154(b) by 0 days.

(21) Appl. No.: 08/894,170

(22) PCT Filed: Jan. 29, 1996

(86) PCT No.: PCT/EP96/00334

§ 371 Date: May 12, 1998

§ 102(e) Date: May 12, 1998

(87) PCT Pub. No.: WO96/23889

PCT Pub. Date: Aug. 8, 1996

(30) Foreign Application Priority Data

Feb. 1, 1995 (DE) ............................................ 195 03 082

(51) Int. Cl.[7] ........................ C12N 15/00; C12N 15/864; C07H 21/04

(52) U.S. Cl. ...................... 435/320.1; 435/455; 435/456; 435/457; 435/69.1; 536/23.1; 536/23.72; 536/24.1; 536/24.2

(58) Field of Search ............................. 424/216.1, 217.1, 424/218.1, 204.1, 205.1, 93.1, 93.2, 93.21, 93.3; 514/44; 435/320.1, 455, 456, 457, 69.1; 536/23.1, 23.72, 24.1, 24.2

(56) References Cited

U.S. PATENT DOCUMENTS

| | | | | |
|---|---|---|---|---|
| 4,650,764 | * | 3/1987 | Temin et al. | 435/240 |
| 5,614,413 | * | 3/1997 | Morrow | 435/320.1 |
| 5,792,462 | * | 8/1998 | Johnston et al. | 424/199.1 |

FOREIGN PATENT DOCUMENTS

| | | |
|---|---|---|
| 0 632 129 | 1/1995 | (EP) . |
| WO 91 04319 | 4/1991 | (WO) . |

OTHER PUBLICATIONS

Orkin and Motulsky, in "Report and Recommendations of the Panel to Assess the NIH Investment in Research on Gene Therapy", Dec. 7, 1995.*

Verma et al., Nature, 387:239–242, 1997.*

Ledley, Pharmaceutical Research, 13:1595–1614, 1996.*

Branch, TIBS, 23:45–50, 1998.*

Agrawal, TIBTECH, 14:376–387, 1996.*

Girard et al., Biologicals, 21:371–377, 1993.*

Trono et al., J. Virology, 62:2291–2299, 1988.*

Vaccine, vol. 13, No. 11, 1995, pp. 1013–1022, XP002005020, Z. Moldoveanu Et Al.: "Immune responses induced by administration of encapsidated poliovirus replicons which express HIV–1 gag and envelope proteins".

Journal of Virology, vol. 67, No. 7, 1993, pp. 3712–3719, XP002005021, D.C. Porter Et Al.: "Encapsidation of genetically engineered poliovirus minireplicons which express HIV–1 gag and pol proteins upon infection".

Journal of Virology, vol. 65, No. 6, 1991, pp. 2875–2883, XP002005022, W.S. Choi Et Al.: "Expression of HIV–1 gag, pol and env proteins fron chimeric HIV–1 poliovirus minireplicons".

Biologicals, vol. 21, 1993, pp. 371–377, XP002005023, M. Girard Et Al.: "Potential use of poliovirus as a vector".

Proceedings of National Academy of Science USA, vol. 84, 1987, pp. 4811–4815, XP00200524 R. Levis Et Al.: "Engineered defective interfering RNA's of Sindbis virus express bacterial chloramphenicol acetyltransferase in avian cells".

Journal of Virology, vol. 67, No. 11, 1993, pp. 6439–6446, XP002005025, P.J. Brendenbeek Et Al.: "Sindbis virus expression vectors: packaging of RNA replicons by using defective helper RNAs".

Nucleic Acids Research, vol. 20, No. 6, 1992, pp. 1293–1299, R.A. Morgan Et Al.: "Retroviral vectors containing putative internal ribosome entry sites: development of a polycistronic gene transfer system and applications to human gene therapy".

Proceedings of National Academy of Science USA, vol. 91, Feb. 1994, pp. 1406–1410, L. Alexander Et Al.: "Poliovirus containing picornavirus Type 1 and/or Type 2 internal ribosomal entry site elements: Genetic hybrids and the expression of a foreign gene".

Haseloff J. Et Al., *Nature*,vol. 334 (1988) pp. 585–591 (Abstract), "Simple RNA enzymes with new and highly specific endoribonuclease activities".

Nellen W. Et Al., *Trends Biochem. Sci.*, vol. 18 (1993) pp. 419–423 (Abstract), "What makes an mRNA anti–sense–itive?".

* cited by examiner

*Primary Examiner*—Deborah J. R. Clark
*Assistant Examiner*—Janet M. Kerr
(74) *Attorney, Agent, or Firm*—Pearne & Gordon LLP

(57) ABSTRACT

The invention relates to a recombinant poliovirus vector and method of making the vector. The recombinant poliovirus vector comprises an RNA polymerase promoter operably linked to a poliovirus nucleic acid sequence which has been altered by removal of the CelII-SnaBI fragment and insertion of a heterologous nucleic acid sequence encoding a protein of interest. The heterologous nucleic acid sequence is flanked on both sides by internal ribosomal entry sites which allow for the expression of the encoded protein of interest and subsequent proteins encoded by the altered poliovirus nucleic acid sequence.

1 Claim, 3 Drawing Sheets

RECOMBINANT POLIOVIRUS VECTOR AND METHOD OF PREPARING THE SAME

BACKGROUND OF THE INVENTION

The invention relates to a recombinant RNA virus vector, to a process for preparing the recombinant RNA virus vector and to its use for preparing a medicament.

The state of the art discloses DNA-dependent systems for expressing proteins in higher eukaryotic cells. For example, the baculovirus system (Bishop DHL, 1990, p. 62–67, Current Opinion in Biotechnology) has been disclosed, which system can, however, only be used in insect cells.

Other eukaryotic systems, such as the Semliki Forest virus system (Liljeström P., Garoff H., 1991, Bio/Technology 9, 1356–1361) are based on an RNA-dependent principle; they cannot be used in vivo on account of their pathogenic potential.

Other systems are based on RNA-encoded viruses, the so-called retroviruses. Expression of foreign genes in these vector systems is not simply translation-dependent; it only takes place following integration into the genomic DNA of the target cell.

The systems which have been mentioned suffer, inter alia, from the disadvantage of integrating into the genome of the respective target cell, something which can have fatal consequences. Retroviral vector systems interact as cDNA in the genome of the target cell. All the constructs which are suitable for effecting transcription have to be provided with regulatory sequences and sequences which are required for processing.

The object of the present invention is to eliminate the disadvantages of the state of the art by means of a novel vector system and to indicate a process for preparing the vector system, and also combinations and possible applications.

This object and expedient further developments are achieved by the features of the claims.

According to the invention, a recombinant RNA virus vector for exerting an effect on cells, in particular for gene therapy, is envisaged whose sequence is altered by removing at least one sequence segment which is necessary for replication competence, and by inserting at least one foreign sequence segment, such that expression of a sequence which is different from the wild type virus can be achieved, can be mediated or can be impeded.

The advantage of this system is, in particular, that no transcription-regulating sequences are required. The novel vector system does not inevitably result in lethal damage to the infected cells and is, on account of its property of primarily transient expression, suitable for in-vivo or ex-vivo administration to a patient.

Suitably, at least one helper cell, helper cell line or helper virus is envisaged. This makes it possible to compensate for the loss in the function of the recombinant RNA virus vector which is caused by removing of at least one sequence segment which is necessary for replication competence. The sequence which is different from the wild type virus can be an antisense sequence or ribozyme sequence for blocking or destroying a viral RNA or DNA molecule.

One embodiment envisages that the sequence is derived from a positive-strand RNA virus, preferably a picornavirus, and that a poliovirus, preferably an attenuated poliovirus, is used as the picornavirus.

This ensures, with high transfection efficiency, that specific RNA sequences are expressed in the cytoplasmic region.

A part of the coding vector sequence, preferably the structural protein-encoding sequence, can be removed and the foreign sequence can be a protein-encoding sequence, in particular a cDNA sequence. In this context, it is advantageous if the recombinant RNA virus vector possesses several internal ribosomal binding sites, preferably those of encephalomyocarditis virus, of poliovirus, of foot and mouth disease virus or of hepatitis A virus.

The helper virus can be capable of being expressed transiently or stably in eukaryotic cells. It is expedient to derive the helper virus from poliovirus.

In one embodiment of the recombinant RNA virus vector, a "suicide gene" can be prepared contrary to the reading direction of the RNA virus vector, and a combination with such sequence elements is envisaged which makes it possible to treat retroviral cells, such as HIV provirus-harboring cells, when a reverse transcriptase and, in particular, a "primer binding site" are present.

According to another solution according to the invention, a process for preparing a novel recombinant RNA virus vector is envisaged in which at least one sequence segment which is necessary for replication competence is removed from the sequence of a preferably double-stranded copy of a wild type virus, at least one foreign sequence segment is inserted and the recombinant RNA virus vector is introduced, for supplementation, into a production cell.

Advantageously, the production cell is a helper cell or a helper cell line. In this case, a helper virus can be introduced into the production cell. It is advantageous if the recombinant RNA virus vector is cloned downstream of a transcription site of a eukaryotic expression vector or downstream of a prokaryotic promoter.

In another embodiment used in the process, the recombinant RNA virus is provided by the helper cell line with an infectious coat, or the helper virus in the production cell supplies an infectious coat.

According to another solution of the object, a kit or compilation of means for implementing the novel process is supplied.

The novel recombinant RNA virus vector can be used to prepare a medicament for transient gene therapy and for treating tumor or autoimmune diseases and for treating wounds. It is also possible to treat retrovirally infected cells, in particular HIV provirus-harboring cells. The use of the novel recombinant RNA virus vector for preparing a medicament for the oral administration of proteins and/or nucleic acids is also of importance.

Since it is not possible to administer the abovementioned medicaments straightforwardly, the invention envisages a compilation of means for administering the medicaments.

A preferred use of the invention is the preparation of clones which encode an immune system-activating gene and which are suitable for being employed as medicaments for the gene therapy of tumor patients. In this context, immunomodulatory substances are to be understood as being interleukins, such as IL-2, IL-10, GMCSF and GCSF, and also immunologically relevant adhesion molecules, such as CD2, CD4, CD8 LFA-1, 4F2, CD40 and CD28, and also their ligands LFA-3, ICAM-1, B7 or CD45. These genes are preferably expressed in recombinant polio viruses in place of the structural proteins which are specific to the virus. The virus proteins which are required in cis are still expressed by using a signal, i.e. an internal ribosomal entry site (IRES), which permits polycistronic consecutive ordering of genes and their expression.

A process for transient gene therapy uses a novel recombinant RNA virus vector for exerting an effect on a host cell, with the expression of a sequence which is different from the wild type virus being achieved, mediated or impeded. Another solution to the above object is achieved by the provision of a kit or a compilation of means for implementing the process.

Expression of immunostimulatory substances in accordance with the invention makes it possible to implement cancer therapy ex vivo and in vivo; the cloning of suicide genes makes it possible to ablate particular cell types, e.g. virus-infected cells in the case of infection with HIV.

One application of the invention for treating autoimmune diseases is the preparation of clones which encode an apoptosis-inducing gene, e.g. the receptor fas, the tumor-suppressing gene p53 or the early adenovirus gene E1A, or encode a so-called suicide gene, and whose surface properties are preferably altered such that they bind especially to cells of the immune system which recognize a particular autoantigen or its epitope and infect these cells.

The use of TNFα, which also elicits apoptotic and necrotic cell death, and TK and CDD, which are known as suicide genes, also aims in this direction. Particular immunologically relevant cells can also be eliminated by inducing anergy by means of depleting primary receptor molecules (e.g. using antisense constructs) or the receptor-associated motifs (Reth motifs). Specificity for target cells of this nature can be achieved by replacing the main antigen of VP1 with the reaction-triggering antigen or by means of specific receptor recognition. In the case of CD4-carrying target cells, the appropriate HIV virus epitope (gp120-V3) is an example of a possible option. Clones of this nature can be administered, preferably systemically, to autoimmune-reactive patients and can invade the autoimmune-reactive cells.

After the cells have been infected, a suicide gene or an apoptosis-inducing gene is expressed in them. This results in higher specificity for the target cells.

Another preferred application of the invention uses genes which lead to the death of the target cells. These genes additionally contain a given specificity for a target cell group, e.g. CD4 or CD26-carrying cells, as a therapeutic agent against an already existing HIV infection.

The destruction of potential HIV virus target cells and of cells into which the HIV virus has integrated leads, particularly in the phase where the virus burden is low, to remission of the infection.

Another preferred application is the expression of anti-inflammatory molecules in the therapy of autoimmunopathies which are in part tissue-destructive.

The process for preparing the novel recombinant RNA virus vector can, in particular, have the following steps:

In a first step, a double-stranded cDNA copy of an RNA virus, preferably an attenuated poliovirus, is provided, prepared, isolated or otherwise obtained (vector DNA). This cDNA copy is preferably present in a prokaryotic replication system.

In a second step, regions of the cDNA construct are excised in accordance with the size of the gene to be cloned. These regions are first and foremost sequences whose function can be replaced in trans, preferably encoded coat proteins, in the case of the poliovirus the genes VP4, VP3, VP2 and/or VP1. The sequences which are required for expression in cis, the protease recognition sites which are required for processing, the internal ribosomal binding sites and the polymerases are retained.

Trans-supplementation with the removed genes is ensured by means of a helper virus or a helper cell line.

The gene which is to be newly expressed in the viral genome is preferably cloned downstream of a suitable internal ribosomal binding site (internal ribosomal entry site, IRES) and provided with its own methionine. The gene to be cloned preferably ends with a stop codon and possesses a further IRES for reinitiating the translation of the subsequent proteins of the virus and a methionine for resuming the translation. The newly added sequence, including the structures just mentioned, usually has about the same sequence length as the fragment which was removed.

The trans-supplementing fragments are made adequately available from a helper virus or, preferably, from a helper cell line, with the expression of toxic products, for example the complete P1 fragment, usually being avoided or restricted.

In one embodiment, the replication-defective recombinant poliovirus genome in a eukaryotic expression vector is transferred into the production cell and expressed in the cell. The recombinant poliovirus RNA can also be present in the production cell following in-vitro transcription and transfection, e.g. electroporation. The recombinant poliovirus RNA is packed into infectious particles in the production cell.

As an alternative to this, a helper virus can also be used which, due to missing genome regions, can no longer be packed into viral particles. In this context, recombination of the helper virus and the recombinant expression virus is preferably to be avoided.

The infectious particles which contain the recombinant expression virus are preferably isolated from the supernatant of the cell culture or from the cytoplasm of infected cells.

The infectious particles, containing the recombinant virus genome, are employed for infecting target cells. In this context, it can be a matter of cells which are maintained in cell culture, of clones, of ex-vivo explants or of systemic or tissue-specific administrations of whole organisms.

EXAMPLES

1. Recombinant poliovirus constructs for the transient expression of interleukin 2.

A fragment of the cDNA of a Sabin 1 poliovirus (vaccine strain) is recloned using its CelII and SnaBI cleavage sites. The cDNA of the human IL-2 gene is inserted into this fragment using adapters and the MunI and SpeI cleavage sites. The IL-2-encoding region is followed by a second internal ribosomal entry site (IRES) from the EMC virus. Stop codons in all three reading frames are located upstream of the second IRES. The resulting subgenomic poliovirus fragment, containing the IL-2 gene and the second IRES, is now inserted into the original construct. Transcription with T7 RNA polymerase yields the recombinant full-length RNA.

The sequences between the first (pos. 3913) and last (pos. 6770) HincII sites are removed from the T7 RNA polymerase-transcribable starting vector. When coinfected, the RNA transcript of this construct supplies the structural proteins which are required for packaging. Cotransfection of the two recombinant RNAs leads to packaging of the recombinant IL-2-encoding full-length RNA into virus coats and consequently to recombinant polioviruses, which are used for infecting tumor cells.

Tumor cells and fibroblasts are isolated by biopsy, cultured in vitro, subjected to lethal irradiation and separated. The tumor cells are deep frozen at −180° C. in aliquots of $10^7$ cells. The fibroblasts are transfected by being coincubated with a recombinant poliovirus. Vaccination is carried out after lethally irradiating the fibroblasts and autologous tumor cells with 10,000 rad. Subcutaneous administration takes place immediately afterwards.

The vaccinations are repeated. As an alternative, tumor therapy can be achieved by administering the attenuated recombinant poliovirus in vivo, in order to directly infect solid tumors, for example.

2. Recombinant poliovirus constructs for transiently expressing the apoptosis-inducing fas gene.

The cDNA of the human fas receptor gene is employed, and the corresponding recombinant full-length poliovirus RNA, and the helper construct, are obtained, in analogy with Example 1. Cotransfection of the two recombinant RNAs gives rise to fas-encoding recombinant polioviruses which are used for infecting cells which are to be ablated. Epitopes of a host-specific antigen, such as that of the acetylcholine receptor in the case of patients suffering from myasthenia gravis, are inserted into the main antigen site of the poliovirus in place of the NSAST-KNKDK (SEQ. ID NO: 1) sequence in the helper construct and lead to preferential uptake of the poliovirus into these autoreactive lymphocytes.

Suitable doses of recombinant virus are administered i.v. after separating the recombinant virus preparation and purifying it by column chromatography.

3. Recombinant poliovirus constructs for the cell type-specific induction of apoptosis.

Recombinant polioviruses encoding the human p53 tumor-suppressing gene are obtained in analogy with Examples 1 and 2. By using a part of the CD4-specific HIV receptor, i.e. the V3 region of the HIV gp120 glycoprotein, the recombinant poliovirus can be conveyed to the same target cells as HIV. Expression of the p53 gene then induces cell death in all CD4-expressing cells and consequently all cells harboring HIV provirus. The epitope of the V3 region of the gp120 protein is inserted, in analogy with Example 2, into the poliovirus main antigen site in place of the NSAST-KNKDK sequence. Recombinant viruses are prepared and administered in analogy with Example 2.

4. Recombinant poliovirus constructs for expressing antiinflammatory molecules in body cells.

Recombinant polioviruses which encode antiinflammatory genes, e.g. the genes which encode IL-10, IL-13, IL-4, TGFβ or the TNFα-T55 receptor, are prepared in Hep-2 cells in analogy with Examples 1 and 2. The resulting recombinant viruses are used to infect isolated body cells.

Following preparation and purification of the recombinant virus preparation, body cells, e.g. synoviocytes or mononuclear cells, which have been freshly isolated from patients are infected in vitro with suitable doses.

BRIEF DESCRIPTION OF THE SEVERAL VIEWS OF THE DRAWING

Exemplary embodiments of the invention are depicted in the drawings.

DESCRIPTION OF THE INVENTION

Figure 1:
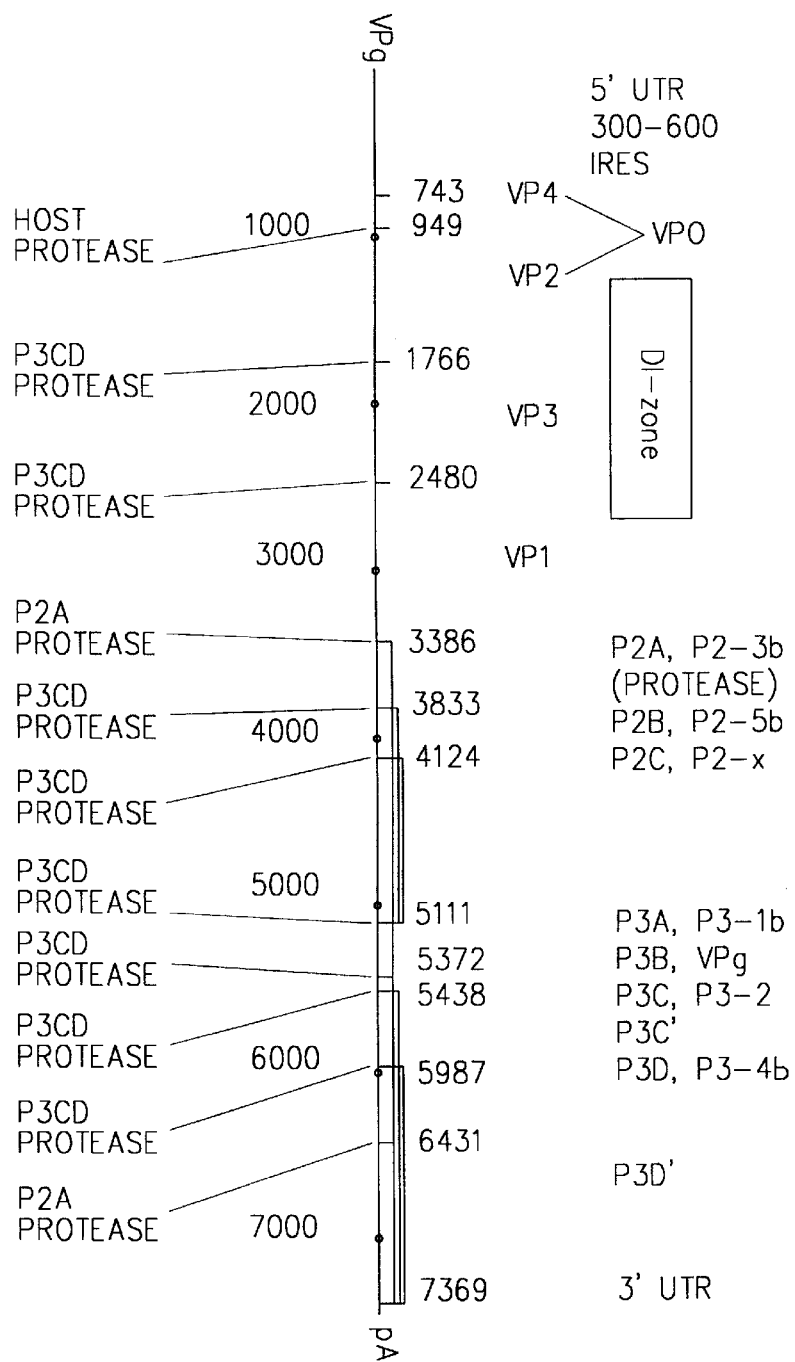
FIG. 1 shows the construction of the Sabin 1 vaccine virus.

In the starting vector shown in FIG. 1, an IRES is located upstream of the polyprotein, which is dissociated, as a result of being processed by different proteases, inter alia the virus-specific proteases P2A and P3D, into a variety of end products. The proteins which are produced in this connection are indicated in the drawing. They can be subdivided into structural proteins (VP1 to VP4) and nonstructural proteins. The former create the coat of the virus while the latter assume a variety of functions in the life cycle of the virus.

Figure 2:
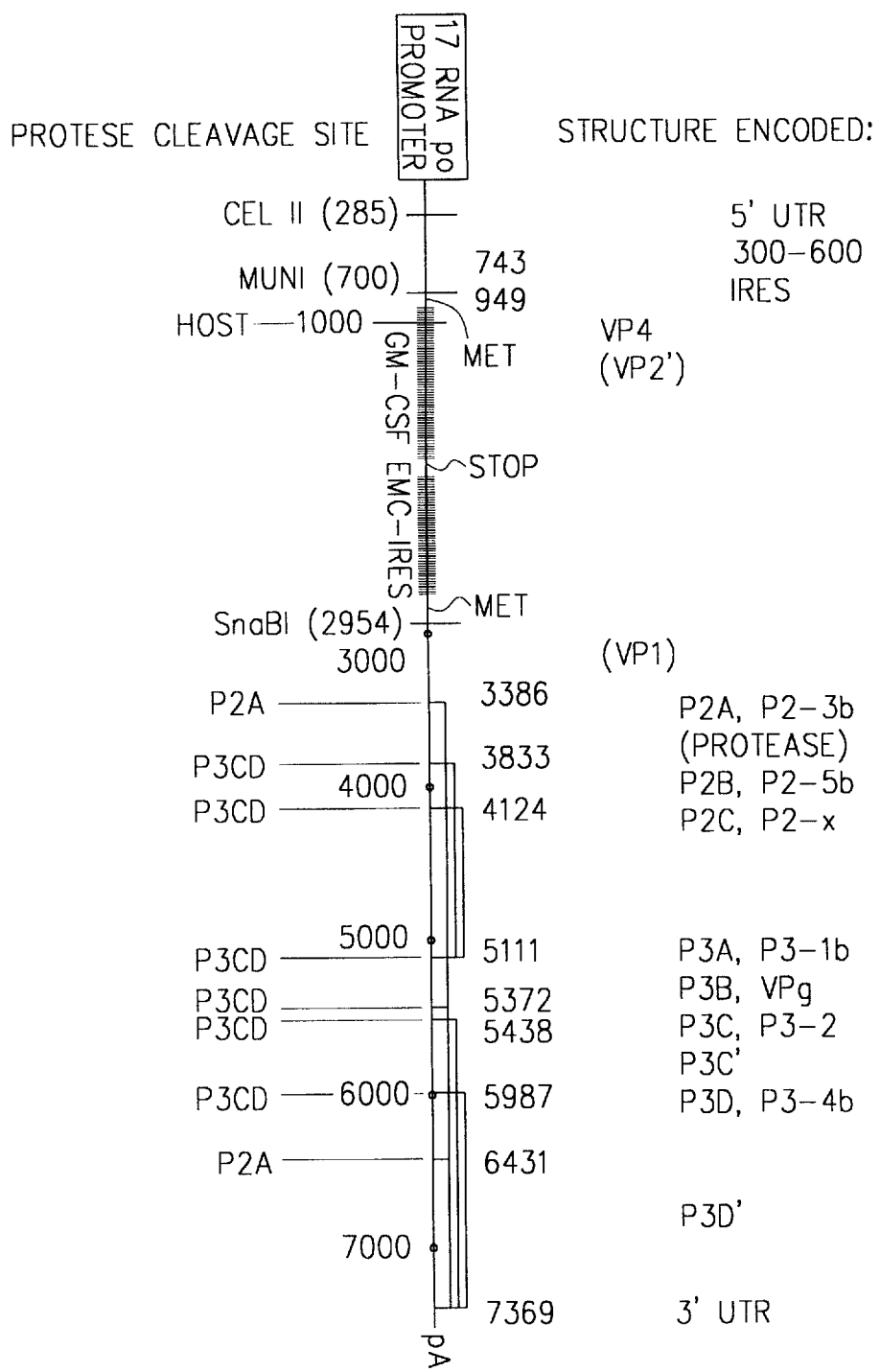
FIG. 2 shows a recombinant virus, taking the example of GM-CSF as the foreign gene.

In the recombinant virus shown in FIG. 2, parts of the structural proteins are replaced with a foreign gene (GM-CSF) and another IRES (EMC IRES).

Figure 3:
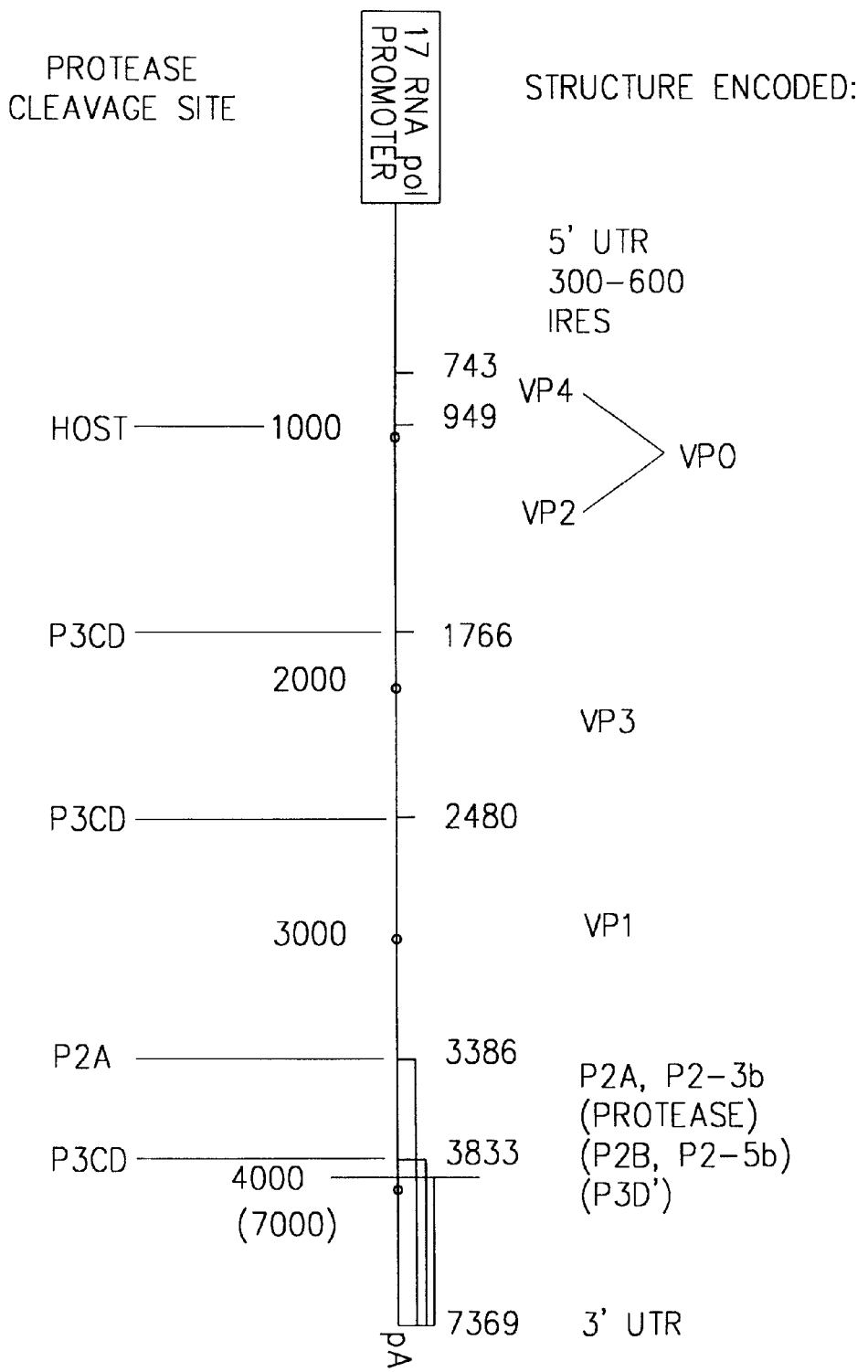
FIG. 3 shows a helper construct.

The helper construct depicted in FIG. 3 provides the structural proteins which are lacking in the vector shown in FIG. 2. However, the helper construct itself is not packaged.

The construction is as follows:

The polyprotein of the starting vector is dissociated, as a result of being processed by different proteases, inter alia the virus-specific proteases P2A and P3D, into a variety of end products. A part of the viral genome (from VP4 to VP1 by way of VP2 and VP3) is replaced with the human GMCSF gene and the subsequent viral proteins are controlled using an additional IRES. In order to introduce a new specificity for these recombinant viruses, the antigenic epitopes of the virus coats on the helper construct, e.g. the main epitope in VP1, can be altered.

What is claimed is:

1. A composition comprising
   (1) a recombinant poliovirus vector, wherein the vector comprises an RNA polymerase promoter operably linked to a poliovirus nucleic acid sequence that has been altered by
      (a) deleting the CelII-SnaBI sequence segment fragment, wherein said fragment encodes the coat proteins, VP1, VP2, VP3, and VP4, and
      (b) inserting therein a heterologous nucleic acid sequence encoding a protein, wherein the heterologous nucleic acid sequence is flanked on both sides by internal ribosomal entry sites (IRES), said IRES allowing for the expression of the encoded protein and for re-initiating expression of subsequent proteins of the altered poliovirus nucleic acid sequence; and
   (2) at least one helper virus for complementation of the coat proteins encoded by the deleted sequence segment fragment.

* * * * *

SEQUENCE LISTING

```
<160> NUMBER OF SEQ ID NOS:   1

<210> SEQ ID NO 1
<211> LENGTH: 10
<212> TYPE: PRT
<213> ORGANISM: Picornavirus
<220> FEATURE:
<221> NAME/KEY: PEPTIDE
<222> LOCATION: (1)..(10)

<400> SEQUENCE: 1

Asn Ser Ala Ser Thr Lys Asn Lys Asp Lys
 1               5                   10
```